(12) United States Patent
Rouyer et al.

(10) Patent No.: US 10,188,408 B2
(45) Date of Patent: Jan. 29, 2019

(54) GLENOID CAVITY BONE PREPARATION SET FOR SETTING A SHOULDER PROSTHESIS, AND METHOD FOR IMPLANTING A SHOULDER PROSTHESIS

(71) Applicants: FOURNITURES HOSPITALIERES INDUSTRIE, Quimper (FR); FH ORTHOPEDICS, Heimsbrunn (FR); Bruce Miller, Ann Arbor, MI (US); DURHAM VALLEY ORTHOPEDIC CONSULTANTS LLC, Durham (PA)

(72) Inventors: Guillaume Rouyer, Quimper (FR); James Hoffmann, Durham, PA (US); Bruce Miller, Ann Arbor, MI (US)

(73) Assignees: FOURNITURES HOSPITALIERES INDUSTRIE, Quimper (FR); FH ORTHOPEDICS, Heimsbrunn (FR); Bruce Miller, Ann Arbor, MI (US); DURHAM VALLEY ORTHOPEDIC CONSULTANTS LLC, Durham, PA (US)

( * ) Notice: Subject to any disclaimer, the term of this patent is extended or adjusted under 35 U.S.C. 154(b) by 241 days.

(21) Appl. No.: 15/296,828

(22) Filed: Oct. 18, 2016

(65) Prior Publication Data
US 2018/0103967 A1    Apr. 19, 2018

(51) Int. Cl.
*A61B 17/17*   (2006.01)
*A61B 17/88*   (2006.01)
(Continued)

(52) U.S. Cl.
CPC ...... *A61B 17/1778* (2016.11); *A61B 17/8897* (2013.01); *A61F 2/30749* (2013.01); *A61F 2/4081* (2013.01); *A61F 2/4612* (2013.01)

(58) Field of Classification Search
CPC ..... A61B 17/17; A61B 17/1778; A61B 17/88; A61B 17/8897; A61F 2/46; A61F 2/40; A61F 2/4081
See application file for complete search history.

(56) References Cited

U.S. PATENT DOCUMENTS

2011/0213372 A1   9/2011   Keefer et al.
2014/0207141 A1   7/2014   Kehres et al.

FOREIGN PATENT DOCUMENTS

EP   2324780 A1   5/2011
FR   2160985 A1   3/2010
FR   2996114 A1   4/2014

*Primary Examiner* — Christopher Beccia
(74) *Attorney, Agent, or Firm* — Cantor Colburn LLP

(57) ABSTRACT

This preparation set comprises a drill guide (31) comprising a bearing surface (33) intended to bear against a glenoid cavity, a passage orifice (35) intended for the passage of a guide pin (36) implanted in the glenoid cavity, and first and second guide orifices (37, 38) each opening into the bearing surface (33) and each intended to guide a drill bit (38) capable of realizing a bone bore in the glenoid cavity, the first and second guide orifices (37, 38) being inclined with respect to the extension axis of the passage orifice (35) and converging in the direction of the bearing surface (33); and a compactor (42) comprising a compaction portion (45) having a generally trapezoidal shape and intended to be impacted against the glenoid cavity so as to form a bone housing in the glenoid cavity, the compactor (42) further including a passage hole (49) extending at least partially in the compaction portion (45) and intended for the passage of the guide pin (36) implanted in the glenoid cavity.

14 Claims, 5 Drawing Sheets

(51) Int. Cl.
*A61F 2/46* (2006.01)
*A61F 2/30* (2006.01)
*A61F 2/40* (2006.01)

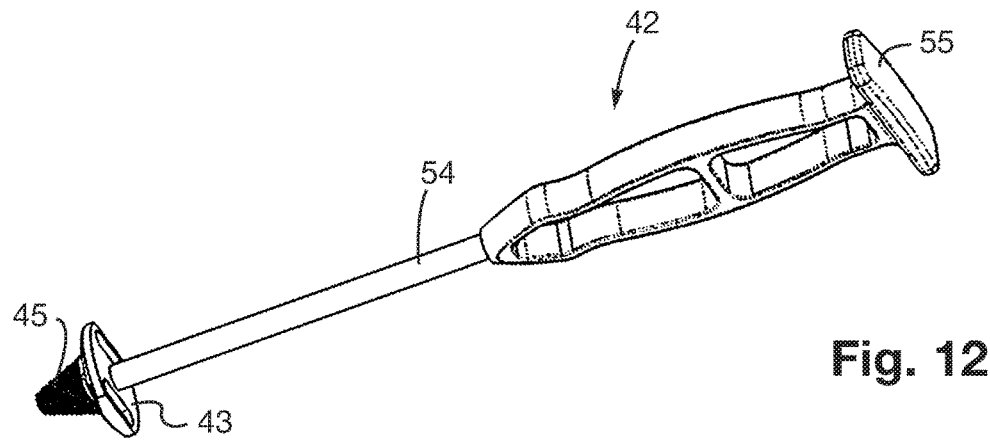
Fig. 12
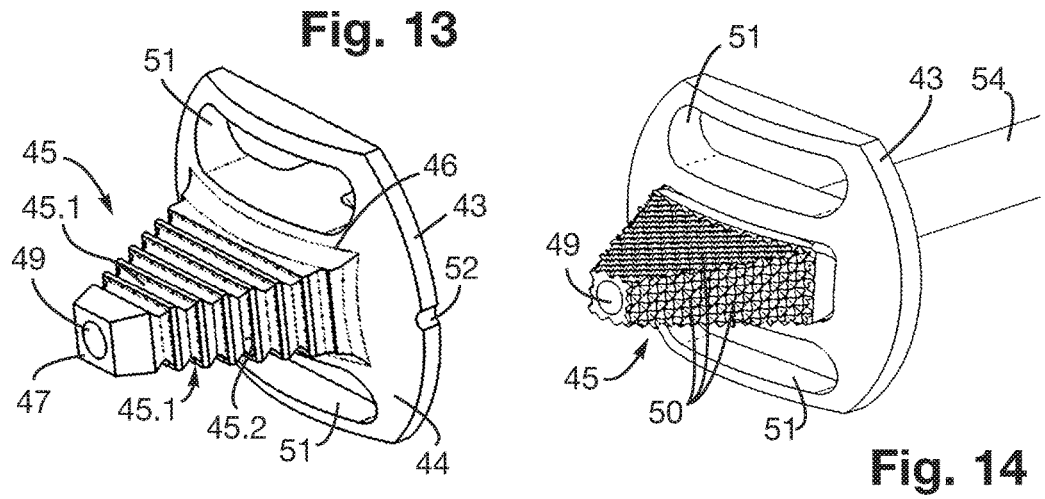
Fig. 13
Fig. 14
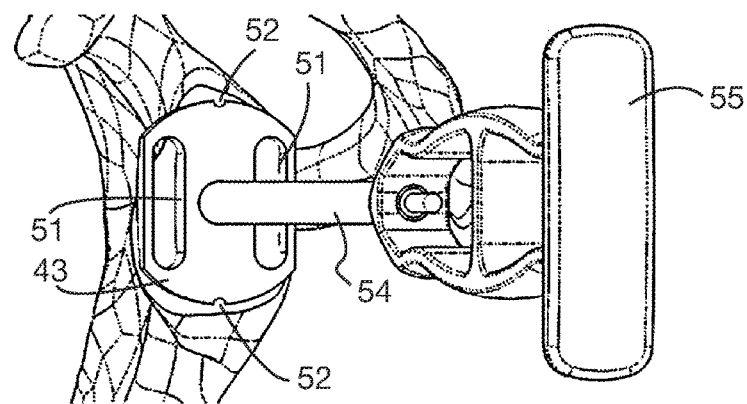
Fig. 15

GLENOID CAVITY BONE PREPARATION SET FOR SETTING A SHOULDER PROSTHESIS, AND METHOD FOR IMPLANTING A SHOULDER PROSTHESIS

TECHNICAL FIELD

The present invention concerns a glenoid cavity bone preparation set for setting a shoulder prosthesis, and more particularly for setting a glenoid base of such a prosthesis.

BACKGROUND

Conventionally, a glenoid base for a shoulder prosthesis with cementless fastening, comprises:
- a support portion configured to be fastened, by means of bone anchoring screws, on a glenoid cavity of a scapula which has been prepared beforehand, the support portion comprising a bearing face intended to bear against the glenoid cavity, and a support face opposite to the bearing face and on which an insert, which is capable of cooperating with a humeral head or with a humeral implant, is intended to be fastened, and
- an anchoring element, also called anchoring keel or stud, extending from the bearing face and intended to be anchored in a bone housing which has been formed beforehand in the glenoid cavity.

Advantageously, the anchoring element has a trapezoidal shape in order to ensure a stable and robust anchoring of the glenoid base in the glenoid cavity.

However, such a configuration of the anchoring element implies a bone preparation of the glenoid cavity which is complex, risky, long and tedious, and which involves the dexterity of the surgeon. Indeed, the realization of the bone housing intended to receive the anchoring element requires in particular placing a cutting guide on the glenoid cavity, the realization of preliminary drills in the glenoid cavity manually using a drilling tool guided by the cutting guide, the realization of incisions in the glenoid cavity using an osteotome guided by the cutting guide, and finishing of the bone housing using the osteotome and one or several compactor(s).

BRIEF SUMMARY

The present invention aims to remedy to these drawbacks.

Hence, the technical problem underlying the invention consists in providing a bone preparation set which has a simple structure and which simplifies and secures the surgical procedure, while ensuring an optimum stability of the glenoid base in the bone.

To this end, the present invention concerns a glenoid cavity bone preparation set for setting a shoulder prosthesis, comprising:
- a drill guide comprising:
  - a bearing surface intended to bear against a glenoid cavity of a scapula which has been prepared beforehand,
  - a passage orifice opening into the bearing surface of the drill guide and intended for the passage of a guide pin implanted in the glenoid cavity, and
  - a first guide orifice and a second guide orifice each opening into the bearing surface of the drill guide and each intended to guide a drill bit capable of realizing a bone bore in the glenoid cavity, the first and second guide orifices being inclined with respect to the extension axis of the passage orifice of the drill guide and converging in the direction of the bearing surface of the drill guide,
- a compactor comprising a compaction portion having a generally trapezoidal shape and intended to be impacted against the glenoid cavity so as to form a bone housing in the glenoid cavity, the compactor further including a passage hole extending at least partially in the compaction portion and intended for the passage of the guide pin implanted in the glenoid cavity.

Such a configuration of the drill guide, and in particular the presence of the passage orifice, allows guaranteeing an optimum positioning of the drill guide with respect to the guide pin, and therefore with respect to the concave surface which has been prepared beforehand in the glenoid cavity, and facilitating and securing the realization of the bone bores in the glenoid cavity using at least one drill bit guided by the first and second guide orifices. Thus, the drill guide according to the present invention allows realizing, easily and accurately, the first removals of bone material of the glenoid cavity, and this strictly within the bulk of the anchoring element of the glenoid base.

Furthermore, the configuration of the compactor, and in particular the presence of the passage hole, guarantees an optimum positioning of the compactor with respect to the guide pin, and therefore with respect to the concave surface which has been prepared beforehand in the glenoid cavity, and therefore facilitates the realization of the bone housing by compacting the cancellous bone of the glenoid cavity.

The set may further present one or more of the following features, considered alone or in combination.

According to one embodiment of the invention, the drill guide includes a guide body including the bearing surface, the passage orifice and the first and second guide orifices.

According to one embodiment of the invention, the bearing surface is convex.

According to one embodiment of the invention, the drill guide includes a gripping handle in order to facilitate its manipulation by a surgeon.

According to one embodiment of the invention, each of the first and second guide orifices extends at an angle of inclination smaller than 45°, with respect to the extension axis of the passage orifice.

According to one embodiment of the invention, the first and second guide orifices are disposed on either side of the passage orifice.

According to one embodiment of the invention, the first and second guide orifices are disposed symmetrically with respect to the extension axis of the passage orifice.

According to one embodiment of the invention, the extension axes of the first and second guide orifices and of the passage orifice extend in the same extension plane.

According to one embodiment of the invention, the compaction portion has a generally isosceles trapezoidal shape.

According to one embodiment of the invention, the compaction portion has a truncated-cone pyramidal shape, for example, with a rectangular base.

According to one embodiment of the invention, the compaction portion has a rectangular cross-section.

According to one embodiment of the invention, the compaction portion extends along an extension direction.

According to one embodiment of the invention, the extension axis of the passage hole is substantially parallel to the extension direction.

According to one embodiment of the invention, the passage hole is centered with respect to the base and to the peak of the compaction portion.

According to one embodiment of the invention, the compaction portion includes a base and a peak opposite to the base, the passage hole opening into the peak of the compaction portion.

According to one embodiment of the invention, the compaction portion includes a plurality of compaction ribs extending transversely to the extension axis of the passage hole. These arrangements allow pushing the compacted bone portions to the bottom of the bone housing while limiting the wedge effects and therefore the risks of fracture of the glenoid cavity during the realization of the bone housing.

According to one embodiment of the invention, the compaction portion includes four lateral faces opposing each other in pairs, each lateral face being provided with a plurality of substantially parallel compaction ribs.

According to one embodiment of the invention, each compaction rib has a triangular cross-section.

According to one embodiment of the invention, the compactor includes a gripping handle in order to facilitate its manipulation by a surgeon.

According to one embodiment of the invention, the gripping handle of the compactor includes a knocking surface on which an impaction force can be transmitted to the compactor.

According to one embodiment of the invention, the compactor comprises an abutment portion including an abutment surface intended to abut against the glenoid cavity, the compaction portion extending from the abutment surface.

According to one embodiment of the invention, the abutment portion includes at least one visualization aperture opening into the abutment surface. Such a configuration of the abutment portion allows the surgeon to visualize the glenoid cavity through the abutment portion when the guide pin is received in the passage hole, which facilitates the surgical procedure.

According to one embodiment of the invention, the compactor includes two visualization apertures disposed on either side of the passage hole.

According to one embodiment of the invention, the abutment portion comprises at least one anterior guide surface which is substantially planar and which is configured to guide a cutting tool capable of realizing an anterior cut on the glenoid cavity.

According to one embodiment of the invention, the compactor includes at least one angular orientation marker allowing orientating the compactor angularly with respect to the guide pin.

According to one embodiment of the invention, the at least one angular orientation marker is disposed on the abutment portion, and for example on a peripheral surface of the abutment portion.

According to one embodiment of the invention, the compactor includes two angular orientation markers diametrically opposed with respect to the passage hole.

According to one embodiment of the invention, the at least one angular orientation marker is formed by a notch or an imprint formed on the abutment portion.

According to one embodiment of the invention, the set further comprises an immobilization element configured to extend in one of the first and second guide orifices and to be inserted in a bone bore formed in the glenoid cavity.

According to one embodiment of the invention, the set further comprises at least one drill bit including a drilling portion configured to be guided in at least one of the first and second guide orifices and to form at least one bone bore in the glenoid cavity, and an abutment portion configured to abut against the drill guide so as to limit the depth of insertion of the at least one drill bit in the glenoid cavity when realizing the at least one bone bore.

According to one embodiment of the invention, the abutment portion of the at least one drill bit is configured to abut against the guide body.

The present invention further concerns a method for implanting a shoulder prosthesis comprising the following steps:
providing a preparation set according to the present invention,
implanting a guide pin in a central portion of the glenoid cavity,
inserting the guide pin in the passage orifice of the drill guide,
positioning the bearing surface of the drill guide against the glenoid cavity,
introducing and guiding a drill bit in the first guide orifice provided on the drill guide so as to realize a first bone bore in the glenoid cavity,
introducing and guiding a drill bit in the second guide orifice provided on the drill guide so as to realize a second bone bore in the glenoid cavity,
retrieving the drill guide from the guide pin,
inserting the guide pin on the passage hole of the compactor,
compacting the cancellous bone of the glenoid cavity using the compaction portion of the compactor so as to form a bone housing.

According to one embodiment of the invention, the implantation method comprises the following steps:
providing a glenoid base for a shoulder prosthesis, the glenoid base including:
a support portion comprising a bearing face intended to bear against the glenoid cavity, and a support face opposite to the bearing face and on which an insert is intended to be fastened which is capable of cooperating with a humeral head or with a humeral implant, and
an anchoring element extending from the bearing face and intended to be anchored in the bone housing formed in the glenoid cavity, the anchoring element having a generally trapezoidal shape,
anchoring the anchoring element of the glenoid base in the bone housing.

According to one embodiment of the invention, the implantation method comprises fastening the glenoid base in the glenoid cavity using bone anchoring screws.

According to one embodiment of the invention, the support portion of the glenoid base is provided with two through passage orifices disposed on either side of the anchoring element, and the step of fastening the glenoid base in the glenoid cavity comprises introducing the bone anchoring screws throughout the through passage orifices provided on the glenoid base.

According to one embodiment of the invention, each through passage orifice is intended to receive the head of the respective bone anchoring screw.

According to one embodiment of the invention, the two through passage orifices are inclined with respect to each other, and are for example inclined with respect to the extension axis of the anchoring element.

According to one embodiment of the invention, the glenoid base includes a fastening portion extending from the bearing face and from an edge of the support portion, the fastening portion comprising a passage orifice.

According to one embodiment of the invention, the implantation method comprises a step carried out before the step of realizing the second bone bore and comprising introducing an immobilization element, such as an immobilization rod, in the first guide orifice provided on the drill guide and in the first bone bore so as to immobilize the rotation of the drill guide.

According to one embodiment of the invention, the implantation method comprises a step carried out before the compaction step and comprising orientating the compactor angularly with respect to the guide pin using angular orientation markers provided on the compactor.

According to one embodiment of the invention, the implantation method comprises a step comprising guiding a cutting tool using an anterior guide surface provided on the compactor so as to realize an anterior bone cut in the glenoid cavity. More particularly, such a cut is intended to receive an anterior fastening leg provided on the glenoid base.

According to one embodiment of the invention, the implantation method comprises a step carried out before the step of implanting the guide pin and comprising milling the glenoid cavity so as to form a concave bearing surface.

According to one embodiment of the invention, the implantation method comprises a step comprising providing a first insert of a first type configured to be fastened on the support portion of the glenoid base, the first insert including an articulating portion having a generally hemispherical shape and being capable of cooperating with a humeral implant, and a second insert of a second type configured to be fastened on the support portion of the glenoid base, the second insert including an articulating portion comprising a concave articulating surface intended to cooperate with a humeral head or with a humeral implant.

According to one embodiment of the invention, the implantation method comprises a step comprising fastening one of the first and second inserts on the support portion of the glenoid base.

According to one embodiment of the invention, the glenoid base includes first fastening means intended to cooperate with complementary fastening means provided on a first insert of a first type, and second fastening means intended to cooperate with complementary fastening means provided on a second insert of a second type.

According to one embodiment of the invention, the second fastening means include a snap-fitting housing opening into the support face and intended to cooperate with a snap-fitting portion provided on the second insert.

According to one embodiment of the invention, the first fastening means include a fastening housing internally delimited at least partially by a truncated-cone shaped surface flaring in the direction of the support face, the fastening housing being intended to receive, by form-fitting, a truncated-cone shaped fastening portion provided on the first insert.

According to one embodiment of the invention, the fastening housing opens into the snap-fitting housing.

According to one embodiment of the invention, the snap-fitting housing and the fastening housing are coaxial.

According to one embodiment of the invention, the fastening housing extends at least partially in the anchoring element.

According to one embodiment of the invention, the first insert is metallic, and is made, for example, of stainless steel.

According to one embodiment of the invention, the first insert includes a bearing portion intended to bear against the support portion.

According to one embodiment of the invention, the first insert includes a fastening element including a generally truncated-cone shaped fastening portion intended to be fastened in the fastening housing of the glenoid base.

According to one embodiment of the invention, the first insert includes a through bore opening into the pole of the convex articulating portion of the first insert, the through bore of the first insert being intended for the passage of a fastening screw capable of cooperating with a threaded bore provided on the glenoid base. For example, the threaded bore is formed in the extension of the fastening housing, and advantageously extends substantially coaxially with the fastening housing.

According to one embodiment of the invention, the through orifice includes a first end opening into the pole of the convex articulating portion of the first insert, and a second end opposite to the first end and opening into the free end of the fastening portion.

According to one embodiment of the invention, the second insert is made of polyethylene.

According to one embodiment of the invention, the articulating portion of the second insert has a generally tray-like shape.

According to one embodiment of the invention, the second insert includes a snap-fitting portion configured to cooperate with the snap-fitting housing provided on the glenoid base. Advantageously, the snap-fitting portion includes at least one snap-fitting rib capable of cooperating with the at least one snap-fitting groove delimited by the snap-fitting housing.

BRIEF DESCRIPTION OF THE DRAWINGS

Anyway, the invention will be better understood from the description which follows, made with reference to the appended schematic drawing representing, as a non-limiting example, an embodiment of this glenoid base.

FIGS. 4 to 18 are perspective views showing different steps of a method for implanting the glenoid base of FIG. 1 in a glenoid cavity of a scapula using a preparation set according to the invention.

DETAILED DESCRIPTION

Figure 1:
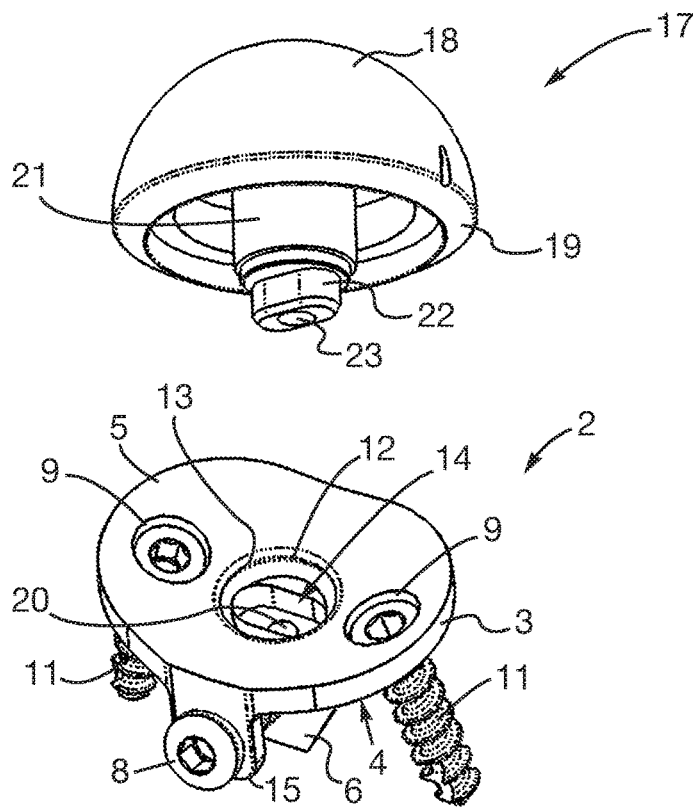
FIG. 1 is a perspective view of a glenoid base and of a first insert which can be secured on the glenoid base.

FIG. 1 represents a glenoid base 2 configured to be fastened on a glenoid cavity of a scapula which has been prepared beforehand. The glenoid base 2 includes a support portion 3 having a generally tray-like shape. More particularly, the support portion 3 includes a bearing face 4 intended to bear against the glenoid cavity, and a support face 5 opposite to the bearing face 4 and on which an insert is intended to be fastened which is capable of cooperating with a humeral head or with a humeral implant. According to the embodiment represented in the figures, the bearing face 4 is convex and the support face 5 is concave.

The glenoid base 2 further includes an anchoring element 6, made, for example, in the form of an anchoring stud, extending from the bearing face 4 and along an extension direction. The anchoring element 6 is intended to be anchored in a bone housing formed beforehand in the glenoid cavity 3. The anchoring element 6 has a generally trapezoidal shape, and more particularly a truncated-cone pyramidal shape with a rectangular base.

According to the embodiment represented in the figures, the anchoring element 6 further includes a through bore 7 inclined with respect to the extension direction of the anchoring element 6 and intended for the passage of a bone anchoring screw 8.

As shown more particularly in FIG. 1, the support portion 3 includes two through passage orifices 9 disposed on either side of the anchoring element 6, and each intended for the passage of a bone anchoring screw 11. Advantageously, the two through passage orifices 9 are inclined with respect to each other, and also with respect to the extension direction of the anchoring element 6. More particularly, each through passage orifice 9 is intended to receive and house the head of the respective bone anchoring screw 11.

The glenoid base 2 further includes a snap-fitting housing 12 centered with respect to the anchoring element 6 and opening into the support face 5. The snap-fitting housing 12 is substantially cylindrical-shaped, and delimits a snap-fitting groove 13.

The glenoid base 2 further includes a fastening housing 14 opening into the snap-fitting housing 12, and having an oblong shape. The fastening housing 14 extends in the extension of the snap-fitting housing 12 so that the snap-fitting housing 12 and the fastening housing 14 are coaxial. Advantageously, the fastening housing 14 extends partially in the anchoring element 6.

The glenoid base 2 also includes a fastening portion 15, for example in the form of a fastening leg, extending from the bearing face 4 and from an edge of the support portion 3. The fastening portion 15 comprises a passage orifice 16 the axis of which is coincident with the axis of the through bore 7 formed on the anchoring element 6. More particularly, the passage orifice 16 is intended to serve as an abutment for the head of the anchoring screw 8 intended to pass throughout the through bore 7.

It should be noted that the glenoid base 2 is provided in a so-called standard version, in which the anchoring element 6 is short, and in a so-called elongate version, in which the anchoring element 6 is long.

FIG. 1 further represents a first insert 17, of a first type, intended to be fastened on the support portion 3 of the glenoid base 2. Advantageously, the first insert 17 is metallic, and may be made, for example, of stainless steel.

The first insert 17 includes a convex articulating portion 18 having a generally hemispherical shape, and being capable of cooperating with a humeral implant. In particular, the articulating portion 18 includes a bearing portion 19 intended to bear against the support face 5 of the support portion 3.

The first insert 17 further includes a fastening element 21 extending from the articulating portion 18. More particularly, the fastening element 21 includes a fastening portion 22 with an oblong section intended to be fastened, by press-fitting, in the fastening housing 14 of the glenoid base 2.

The first insert 17 also includes a through bore 23 including a first end opening into the pole of the articulating portion 18, and a second end opposite to the first end and opening into the free end of the fastening portion 22. The through bore 23 of the first insert 17 is intended for the passage of a fastening screw capable of cooperating with a threaded bore 20 provided on the glenoid base 2 so as to secure the fastening of the first insert 17 on the glenoid base 2. Advantageously, the threaded bore 20 extends in the extension of the fastening housing 14, and coaxially with the fastening housing 14.

Figure 2:
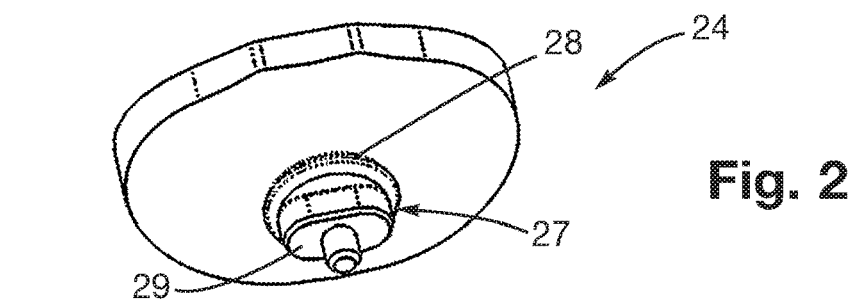
FIG. 2 is a bottom perspective view of a second insert which can be secured on the glenoid base of FIG. 1.
Figure 3:
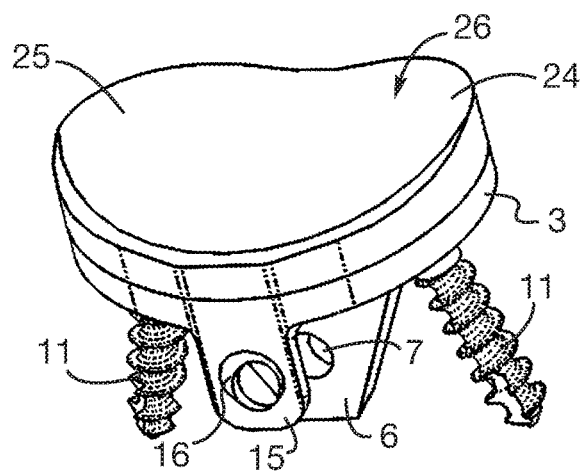
FIG. 3 is a perspective view showing the second insert secured on the glenoid base of FIG. 1.
Figure 4:
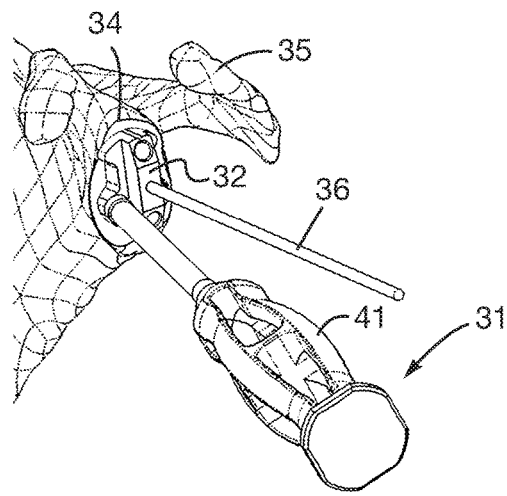

FIGS. 2 and 3 represent a second insert 24, of a second type, intended to be fastened on the support portion 3 of the glenoid base 2. Advantageously, the second insert 24 is made of a plastic material, such as a polymer, and may be made, for example, of polyethylene.

The second insert 24 includes an articulating portion 25 having a generally tray-like shape, and comprising a concave articulating surface 26 intended to cooperate with a humeral head or with a humeral implant.

The second insert 24 further includes a snap-fitting portion 27 configured to cooperate with the snap-fitting housing 12 provided on the glenoid base 2.

Advantageously, the snap-fitting portion 27 includes a snap-fitting rib 28 capable of cooperating by snap-fitting with the snap-fitting groove 13 delimited by the snap-fitting housing 12.

According to the embodiment represented in the figures, the second insert 24 includes a fastening portion 29 with an oblong section intended to be fastened, by press-fitting, in the fastening housing 14 of the glenoid base 2.

FIGS. 4 to 11 represent a drill guide 31 comprising a guide body 32 including a convex bearing surface 33 (see FIG. 11) intended to bear against a glenoid cavity 34 of a scapula 35.

The guide body 32 further comprises a central passage orifice 35 opening into the bearing surface 33 and intended for the passage of a guide pin 36 implanted in the glenoid cavity 34.

The guide body 32 also comprises a first guide orifice 37 and a second guide orifice 38 each opening into the bearing surface 33 and each intended to guide a drill bit 39 capable of realizing bone bores in the glenoid cavity 34. More particularly, the drill bit 39 comprises a drilling portion 39.1 configured to be guided in each of the first and second guide orifices 37, 39, and an abutment portion 39.2 configured to abut against the guide body 32 so as to limit the depth of insertion of the drill bit 39 in the glenoid cavity 34 when realizing the bone bores.

The first and second guide orifices 37, 38 are disposed on either side of the passage orifice 35 and symmetrically with respect to the extension axis of the passage orifice 35. Furthermore, the first and second guide orifices 37, 38 are inclined with respect to each other and with respect to the extension axis of the passage orifice 35. In addition, the first and second guide orifices 37, 38 converge in the direction of the bearing surface 33. Advantageously, each of the first and second guide orifices 38, 39 extends at an angle of inclination smaller than 45°, with respect to the extension axis of the passage orifice 35.

Figure 5:
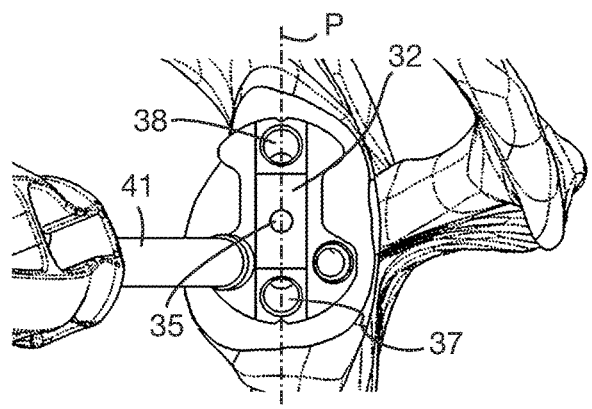
Figure 6:
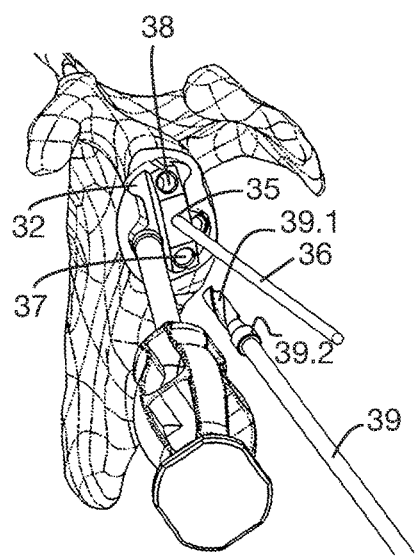
Figure 7:
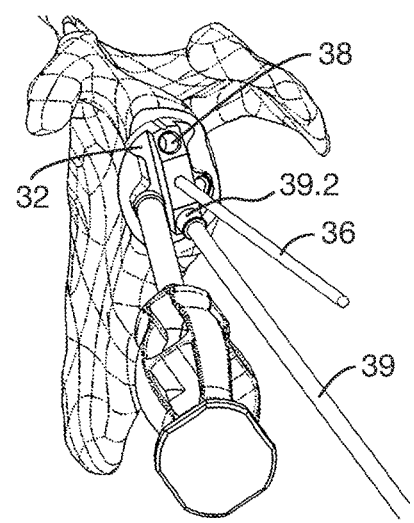
Figure 8:
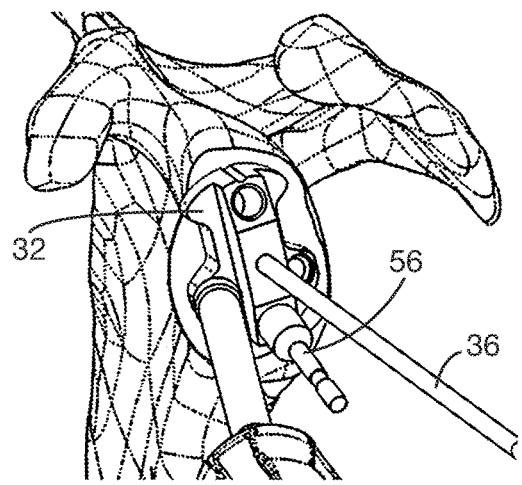
Figure 9:
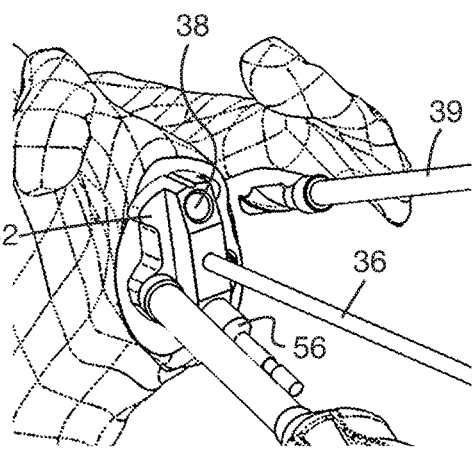
Figure 10:
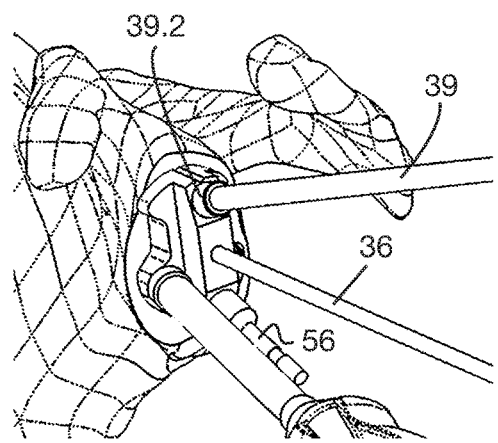
Figure 11:
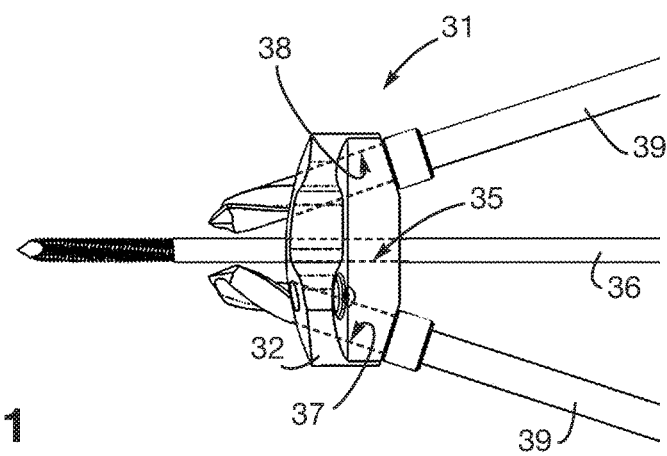
Figure 16:
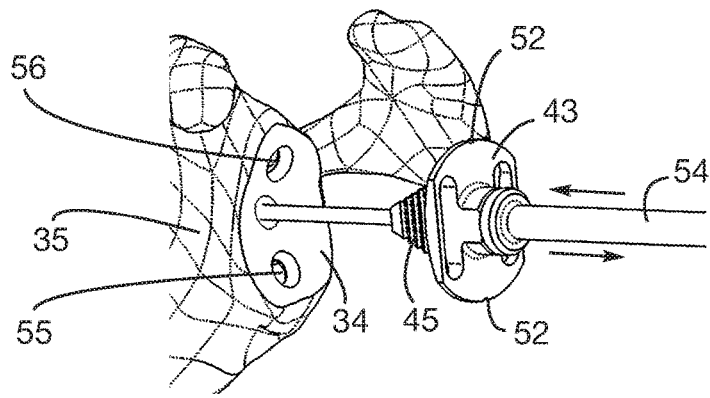
Figure 17:
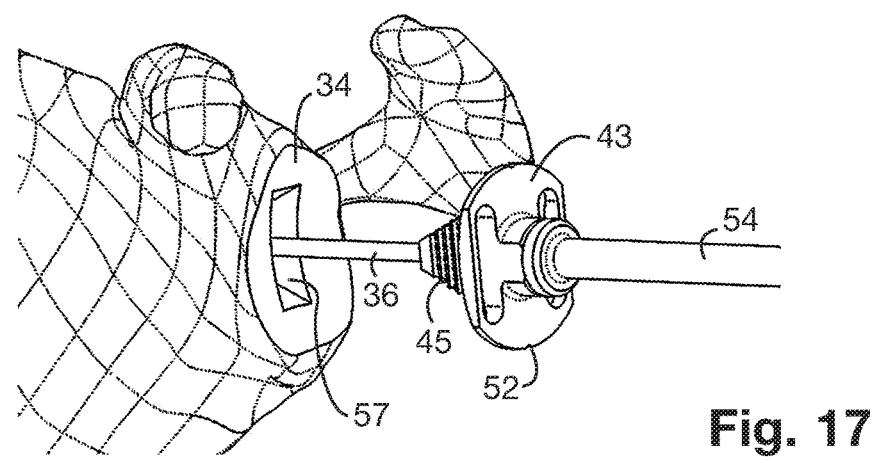
Figure 18:
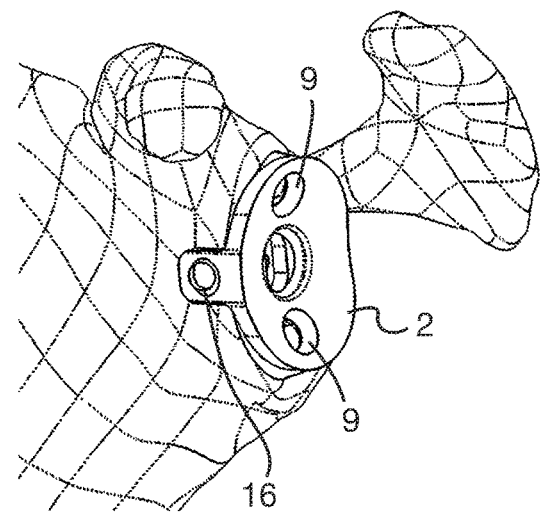

Advantageously, the extension axes of the first and second guide orifices 37, 38 and of the passage orifice 35 extend in the same extension plane P (see FIG. 5).

The drill guide 31 also includes a gripping handle 41 in order to facilitate its manipulation by a surgeon. More particularly, the gripping handle 41 is secured to the guide body 32.

FIGS. 12 to 17 represent a compactor 42 comprising an abutment portion 43 including a convex abutment surface 44 intended to abut against the glenoid cavity 34, and a compaction portion 45 extending from the abutment surface 44 and intended to be impacted against the glenoid cavity 34 so as to form a bone housing in the glenoid cavity 34.

More particularly, the compaction portion 45 has a truncated-cone pyramidal shape with a rectangular base. Thus, the compaction portion 45 includes four lateral faces 45.1, 45.2 opposing each other in pairs, as well as a base 46 and a peak 47 opposite to the base 44.

According to the embodiment represented in FIG. 13, the compaction portion 45 further includes a plurality of compaction ribs 48 extending perpendicularly to the extension direction of the compaction portion 45. More particularly, each lateral face 45.1, 45.2 of the compaction portion 45 is provided with a plurality of compaction ribs 48 substantially parallel and shifted axially with respect to each other. Advantageously, each compaction rib 48 has a triangular cross-section.

According to a variant represented in FIG. 14, each lateral face 45.1, 45.2 of the compaction portion 45 may include, instead of the compaction ribs 48, compaction spikes 50, for example diamond spikes.

The compactor 42 further includes a passage hole 49, for example in the form of a passage channel, intended for the passage of the guide pin 36 implanted in the glenoid cavity 34. The passage hole 49 extends at least partially in the compaction portion 45 and substantially parallel to the extension direction of the compaction portion 45. Advantageously, the passage hole 49 is centered with respect to the base 46 and to the peak 47 of the compaction portion 45, and opens into the peak 47 of the compaction portion 45.

Advantageously, the abutment portion 43 also includes one or several visualization aperture(s) 51 opening into the abutment surface 44. Such a configuration of the abutment portion 43 allows the surgeon to visualize the glenoid cavity 34 through the abutment portion 43 when the guide pin 36 is received in the passage hole 49, which facilitates the surgical procedure. According to the embodiment represented in the figures, the compactor 42 includes two visualization apertures 51 disposed on either side of the passage hole 49.

The compactor 42 also includes one or several angular orientation marker(s) 52 allowing orientating the compactor 42 angularly with respect to the guide pin 36. According to the embodiment represented in the figures, the compactor 42 includes two angular orientation markers 52 diametrically opposed with respect to the passage hole 49 and formed on a peripheral surface of the abutment portion 43.

According to the embodiment represented in the figures, the abutment portion 43 further comprises an anterior guide surface 53 which is substantially planar and which is configured to guide a cutting tool capable of realizing an anterior cut on the glenoid cavity 34.

The compactor 42 further includes a gripping handle 54 in order to facilitate its manipulation by a surgeon. Advantageously, the gripping handle 54 includes a knocking surface 55 on which an impaction force can be transmitted to the compactor 42.

Advantageously, the passage hole 49 extends at least partially through the gripping handle 54.

A method for implanting a glenoid base will now be described, more particularly with reference to FIGS. 4 to 18.

Such an implantation method comprises the following steps:
implanting the guide pin 36 in a central portion of the glenoid cavity 34,
inserting the guide pin 36 in the passage orifice 35 of the drill guide 31,
making the guide body 32 slide along the guide pin 36 in the direction of the glenoid cavity 34,
positioning the bearing surface 33 of the drill guide 31 against the glenoid cavity 34 (see FIG. 4),
introducing and guiding the drill bit 39 in the first guide orifice 37 provided on the drill guide 31 so as to realize a first bone bore 55 in the glenoid cavity 34 (see FIGS. 6, 7 and 16),
extracting the drill bit 39 out from the first guide orifice 37,
introducing an immobilization element 56, such as an immobilization rod, in the first guide orifice 37 provided on the drill guide 31 and in the first bone bore 55 so as to immobilize the rotation of the drill guide 31 (see FIG. 8),
introducing and guiding the drill bit 39 in the second guide orifice 38 provided on the drill guide 31 so as to realize a second bone bore 56 in the glenoid cavity 34 (see FIGS. 9, 10 and 16),
extracting the drill bit 38 out from the second guide orifice 38,
retrieving the immobilization element 56 out from the first guide orifice 37,
retrieving the drill guide 31 by making the guide body 32 slide along the guide pin 36,
inserting the guide pin 36 in the passage hole 49 of the compactor 42 (see FIG. 16),
making the compaction portion 45 slide along the guide pin 36 in the direction of the glenoid cavity 34,
orientating the compactor 42 angularly with respect to the guide pin 36 using the angular orientation markers 52 so that the angular orientation markers 52 are aligned with the first and second bone bores 55, 56 (see FIG. 14),
compacting the cancellous bone of the glenoid cavity 34 using the compaction portion 45 so as to form a bone housing 57 in the glenoid cavity 34 (see FIGS. 16 and 17),
guiding a cutting tool using the anterior guide surface 53 so as to realize an anterior bone cut in the glenoid cavity 34 so as to allow fastening the fastening portion 15 of the glenoid base 2,
retrieving the compactor 42 by making the compaction portion 45 slide along the guide pin 36,
retrieving the guide pin 36,
anchoring the anchoring element 6 of the glenoid base 2 in the bone housing 57 (see FIG. 18),
fastening the glenoid base 2 using the bone anchoring screws 8, 11,
fastening one of the first and second inserts 17, 24 on the support portion 3 of the glenoid base 2.

It goes without saying that the invention is not limited to the sole embodiment of this preparation set, described hereinabove as example, but it encompasses on the contrary all variants thereof.

The invention claimed is:

1. A glenoid cavity bone preparation set for setting a shoulder prosthesis, comprising:
a drill guide comprising:
a bearing surface intended to bear against a glenoid cavity of a scapula which has been prepared beforehand,
a passage orifice opening into the bearing surface of the drill guide and intended for the passage of a guide pin implanted in the glenoid cavity, and
a first guide orifice and a second guide orifice each opening into the bearing surface of the drill guide and each intended to guide a drill bit capable of realizing a bone bore in the glenoid cavity, the first and second guide orifices being inclined with respect to an extension axis of the passage orifice of the drill guide and converging in the direction of the bearing surface of the drill guide,
a compactor comprising a compaction portion having a generally trapezoidal shape and intended to be impacted against the glenoid cavity so as to form a bone housing in the glenoid cavity, the compactor further including a passage hole extending at least partially in the compaction portion and intended for the passage of the guide pin implanted in the glenoid cavity.

2. The set according to claim 1, wherein the first and second guide orifices are disposed on either side of the passage orifice.

3. The set according to claim 1, wherein extension the axes of the first and second guide orifices and of the passage orifice extend in a same extension plane.

4. The set according to claim 1, wherein the compaction portion includes a base and a peak opposite to the base, the passage hole opening into the peak of the compaction portion.

5. The set according to claim 1, wherein the compaction portion includes a plurality of compaction ribs extending transversely to the extension axis of the passage hole.

6. The set according to claim 5, wherein the compaction portion includes four lateral faces opposing each other in pairs, each lateral face being provided with a plurality of substantially parallel compaction ribs.

7. The set according to claim 1, wherein the compactor comprises an abutment portion including an abutment surface intended to abut against the glenoid cavity, the compaction portion extending from the abutment surface.

8. The set according to claim 7, wherein the abutment portion includes at least one visualization aperture opening into the abutment surface.

9. The set according to claim 7, wherein the abutment portion comprises at least one anterior guide surface which is substantially planar and which is configured to guide a cutting tool capable of realizing an anterior cut on the glenoid cavity.

10. The set according to claim 1, wherein the compactor includes at least one angular orientation marker allowing orientating the compactor angularly with respect to the guide pin.

11. The set according to claim 1, which further comprises an immobilization element configured to extend in one of the first and second guide orifices and to be inserted in a bone bore formed in the glenoid cavity.

12. The set according to claim 1, which further comprises at least one drill bit including a drilling portion configured to be guided in at least one of the first and second guide orifices and to form at least one bone bore in the glenoid cavity, and an abutment portion configured to abut against the drill guide so as to limit the depth of insertion of the at least one drill bit in the glenoid cavity when realizing the at least one bone bore.

13. A method for implanting a shoulder prosthesis comprising the following steps:
   providing a bone preparation set according to claim 1,
   implanting a guide pin in a central portion of the glenoid cavity,
   inserting the guide pin in the passage orifice of the drill guide,
   positioning the bearing surface of the drill guide against the glenoid cavity,
   introducing and guiding a drill bit in the first guide orifice provided on the drill guide so as to realize a first bone bore in the glenoid cavity,
   introducing and guiding a drill bit in the second guide orifice provided on the drill guide so as to realize a second bone bore in the glenoid cavity,
   retrieving the drill guide from the guide pin,
   inserting the guide pin on the passage hole of the compactor,
   compacting a cancellous bone of the glenoid cavity using the compaction portion of the compactor so as to form a bone housing.

14. The implantation method according to claim 13, which comprises the following steps:
   providing a glenoid base for a shoulder prosthesis, the glenoid base including:
   a support portion comprising a bearing face intended to bear against the glenoid cavity, and a support face opposite to the bearing face and on which an insert, which is capable of cooperating with a humeral head or with a humeral implant, is intended to be fastened, and
   an anchoring element extending from the bearing face and intended to be anchored in the bone housing formed in the glenoid cavity, the anchoring element having a generally trapezoidal shape,
   anchoring the anchoring element of the glenoid base in the bone housing.

* * * * *